United States Patent
Mühlbauer et al.

(10) Patent No.: US 6,499,630 B2
(45) Date of Patent: Dec. 31, 2002

(54) SYSTEM FOR THE RELEASE OF EQUAL PROPORTIONS OF TWO FLOWABLE SUBSTANCES, ESPECIALLY FOR DENTAL PURPOSES

(75) Inventors: Wolfgang Mühlbauer, Hamburg (DE); Hans Hörth, Hamburg (DE); Frauke Röbel, Hamburg (DE)

(73) Assignee: Ernst Muhlbauer KG, Hamburg (DE)

( * ) Notice: Subject to any disclaimer, the term of this patent is extended or adjusted under 35 U.S.C. 154(b) by 0 days.

(21) Appl. No.: 09/964,080

(22) Filed: Sep. 25, 2001

(65) Prior Publication Data

US 2002/0042591 A1 Apr. 11, 2002

(30) Foreign Application Priority Data

Sep. 25, 2000 (EP) .............................................. 00120858

(51) Int. Cl.[7] .................................................. B67D 5/52
(52) U.S. Cl. ..................................... 222/137; 222/145.6
(58) Field of Search ................................ 222/135, 137, 222/145.1, 145.5, 145.6, 386

(56) References Cited

U.S. PATENT DOCUMENTS

| | | | |
|---|---|---|---|
| 4,260,077 A | | 4/1981 | Schroeder |
| 4,874,368 A | * | 10/1989 | Miller et al. .................. 222/137 |
| 4,979,942 A | * | 12/1990 | Wolf et al. .................. 222/137 |
| 5,104,375 A | | 4/1992 | Wolf et al. |
| 5,290,259 A | * | 3/1994 | Fischer ........................ 604/218 |
| 5,582,596 A | * | 12/1996 | Fukunaga et al. ........... 604/191 |
| 6,047,861 A | * | 4/2000 | Vidal et al. .................. 222/137 |
| 6,234,994 B1 | * | 5/2001 | Zinger .......................... 222/137 |
| 6,286,722 B1 | * | 9/2001 | Fischer et al. ............... 222/137 |
| 6,311,869 B1 | * | 9/2001 | Horth et al. ................. 222/137 |

* cited by examiner

Primary Examiner—Joseph A. Kaufman
(74) Attorney, Agent, or Firm—Alix, Yale & Ristas, LLP

(57) ABSTRACT

System for the release of equal proportions of two flowable substances having two syringes, of which at least one is also used alone or in combination with other syringes, especially for dental purposes. In order to enable the connected syringes to be used irrespective of the current piston position, detachable devices (14, 22) for coupling the syringe bodies (1, 11) and devices (30) for coupling the syringe pistons, irrespective of their current position, are provided (FIG. 1).

20 Claims, 4 Drawing Sheets

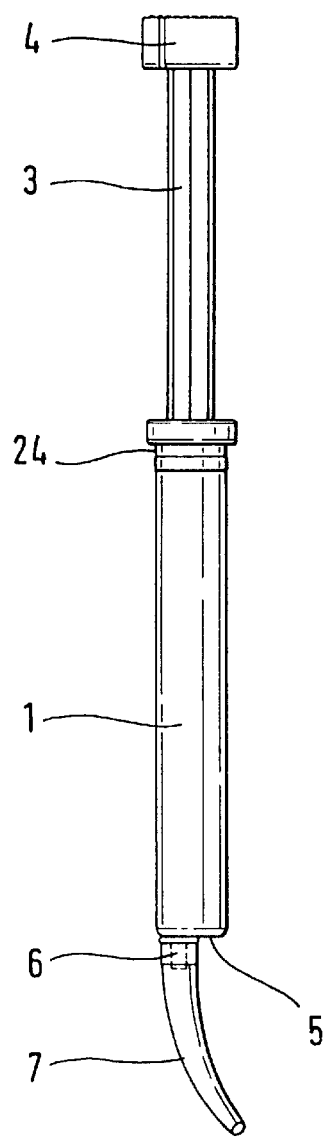
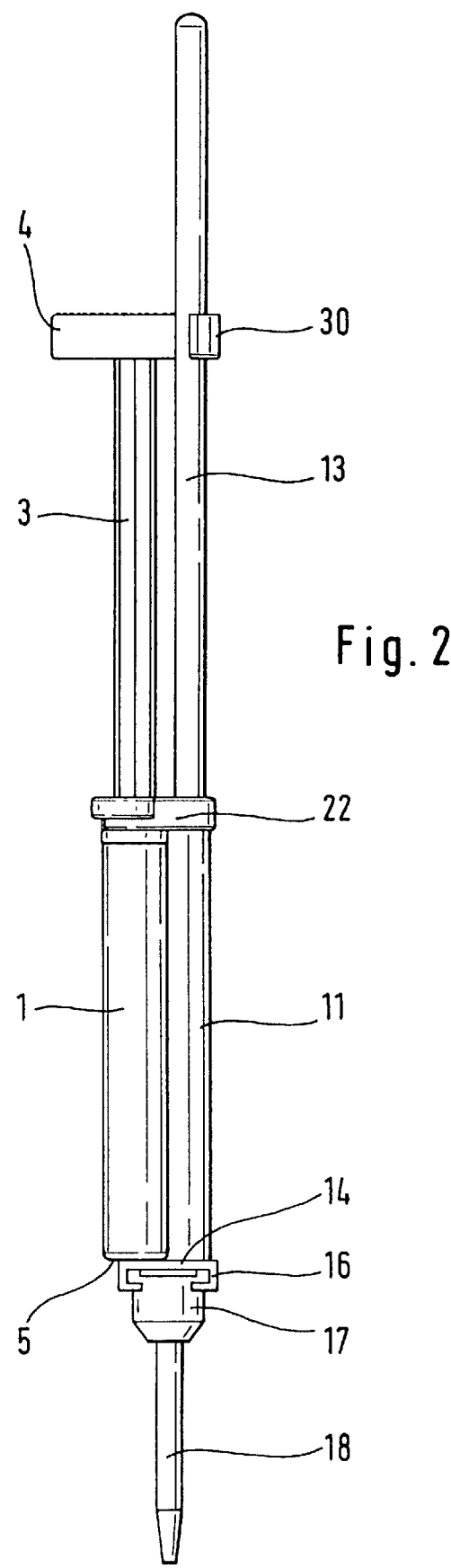
Fig.1
Fig.2

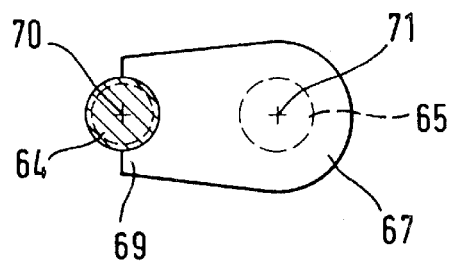
Fig. 10
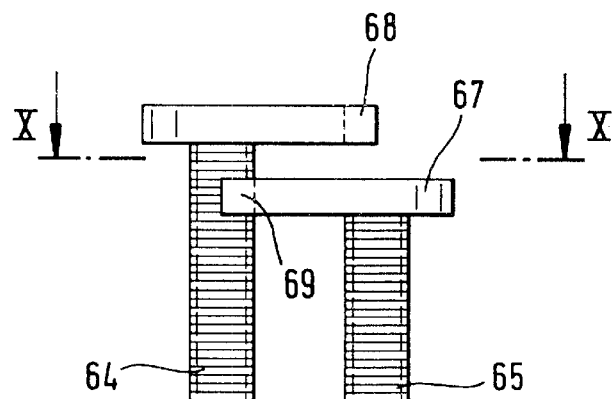
Fig. 11
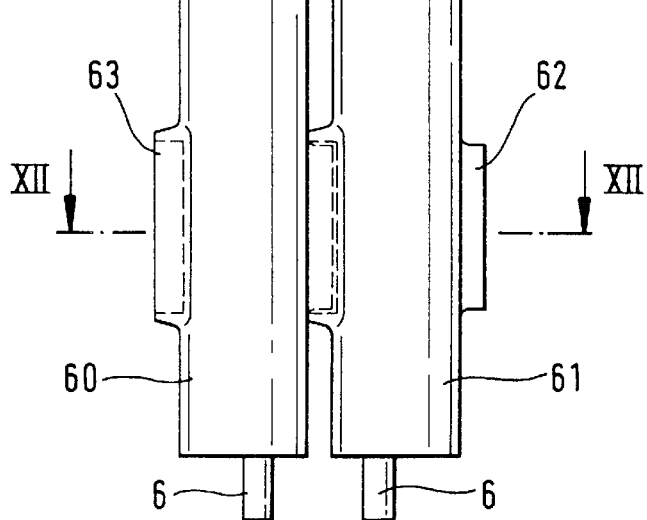
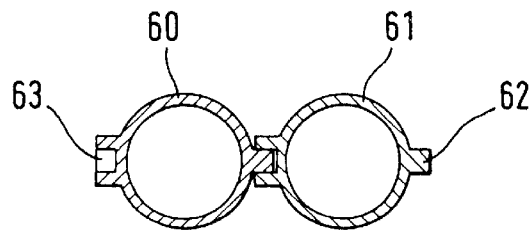
Fig. 12

SYSTEM FOR THE RELEASE OF EQUAL PROPORTIONS OF TWO FLOWABLE SUBSTANCES, ESPECIALLY FOR DENTAL PURPOSES

BACKGROUND OF THE INVENTION

If it is desired to produce a portion of a mixture of two flowable components which must be in a particular quantitative ratio to one another, two piston-and-cylinder syringes can be used which are coupled to one another for the joint movement of their pistons. The quantitative ratio of the components is then determined by the cross-sectional ratio of the pistons. An important field of application of such coupled syringes is in dental technology, specifically the initial mixing of multicomponent resins as fillers or of an impression compound. Known systems for the release of equal proportions of flowable substances comprise an appliance in which the pistons of the two syringes are synchronously advanced (EP-B-0 492 413, EP-A-1 010 401, WO 91/05 731). In these, not only are the syringe bodies rigidly held side by side but, by means of push rods connected to one another, the pistons are likewise rigidly connected to one another, each adopting the same position in the associated syringe bodies. It follows also that the states of emptying of the two syringe bodies must always coincide. This causes no problem if one component is always used with the same other component and the syringes containing them are therefore only used together. However, there are cases in which this condition is not satisfied. For example, there are dental resins which as a rule are used without a second component and are then cured by means of radiation, but which exceptionally are also used in mixtures containing a curing agent as the second component. In these cases, it has hitherto been necessary to meter the components individually and mix them by hand. Systems are also known in which two syringes, which contain components assigned to one another, are prepared separately and brought together in specific cases for application in a single appliance (WO 91/05 371, U.S. Pat. No. 4,260,077, U.S. Pat. No. 5 104 375). A necessary condition here is that the levels of filling coincide.

SUMMARY OF THE INVENTION

It would be expedient, where the basic component remains the same and is to be used variably in specific cases with or without an additional component, always to be able to use the same syringe, while the syringes for the additional components can be combined therewith as desired and without regard to their random level of filling. It is an object of the invention to provide a system which permits this.

According to the claims, provision is made for both the syringe bodies and the syringe pistons to be able to be rigidly coupled to one another in the direction of advance by releasable coupling devices irrespective of the current piston position. The coupling devices are so formed that the pistons and/or the syringe bodies can be connected to one another (in the direction of advance) in any desired relative position. A system is preferred in which the syringe bodies can be coupled to one another only in a predetermined relative position but the piston rods belonging to the pistons can be coupled to one another in any desired relative position.

The devices for coupling the syringe bodies to one another may be provided separately from the latter. It is more expedient, however, to provide the syringe bodies themselves with mutually fitting coupling devices. They are expediently fixedly connected to at least one thereof or form a fixed component thereof.

The syringe bodies are generally provided at their front ends with a release pipe. If two components are released together, they are in general processed together, and may or may not also be released jointly from a mixing device. It is therefore expedient to form the coupling device for the syringe bodies in such a way that their release pipes are located close together or at least in a defined position relative to one another. In order to ensure this in the direction of advance, provision may be made, according to the invention, for a part of the coupling device provided on one of the two syringe bodies or to be attached to be formed as a stop for a frontal surface of the other syringe body, counter to the direction of advance. In order to ensure this transversely to the direction of advance, the device for coupling the syringe bodies may be so formed that the release pipe of at least one of the two syringe bodies may thereby be localized transversely to the direction of advance. The transverse distance between the release pipes is especially important if a nozzle for the joint release, with or without mixing, of the two substances. According to the invention, the coupling device can be provided with a device for the releasable retention of such a nozzle. For the relative securing of the syringe bodies in the direction of advance, the single stop mentioned may be sufficient. More expediently, however, a second stop is provided additionally or instead and additionally secures the syringe body, which is secured in one direction by the front stop, in the other direction also. This is expediently achieved by a more rearward part of the coupling device.

In order for the syringe bodies to remain in the coupled position, suitable fixing means are expediently provided, these being formed, for example, by a snap-fit mounting.

The syringe bodies are expediently coupled to one another in parallel, so that the mutually coupled sections of the piston rods remain at a constant distance from one another during their advance.

The device for coupling the piston rods may be fixedly disposed at the end of one of the two piston rods. This means that the other piston rod has to be approximately twice as long to ensure that an effective coupling connection can be formed even if the syringe provided with the coupling device for the piston rods is still full but the other is nearly empty. This does not apply if a separate coupling is used or if both piston rods bear a coupling device.

The coupling device for the piston rods is expediently formed as a clamp, in order, under the action of the force of a spring closing it, to enclose the piston rod in question so firmly that a sufficient friction is generated for entrainment in the direction of advance. However, closure devices may also be provided thereon which generate this coupling force.

In order to permit a firm grip of the clamp on the piston rod, the surfaces of the two are expediently formed to engage into one another. For this, even a roughening is sufficient, the peaks of the roughnesses thereof engaging randomly into the troughs of the roughnesses of the respective other surface. The surfaces may however also be regularly gridded or ribbed (transversely to the direction of advance). Such structures should be so fine that they do not lead to a substantial change in the existing statuses of the pistons when the clamps are applied.

BRIEF DESCRIPTION OF THE DRAWINGS

The invention is explained in detail below with reference to the drawings, which illustrate advantageous examples of embodiment, and in which:

FIG. 1 shows a first syringe for general use,

FIG. 2 shows the first syringe assembled with a second syringe,

FIGS. 10 to 12 show a further embodiment of a device for connecting two piston rods.

DETAILED DESCRIPTION OF PREFERRED EMBODIMENT

Figure 3:
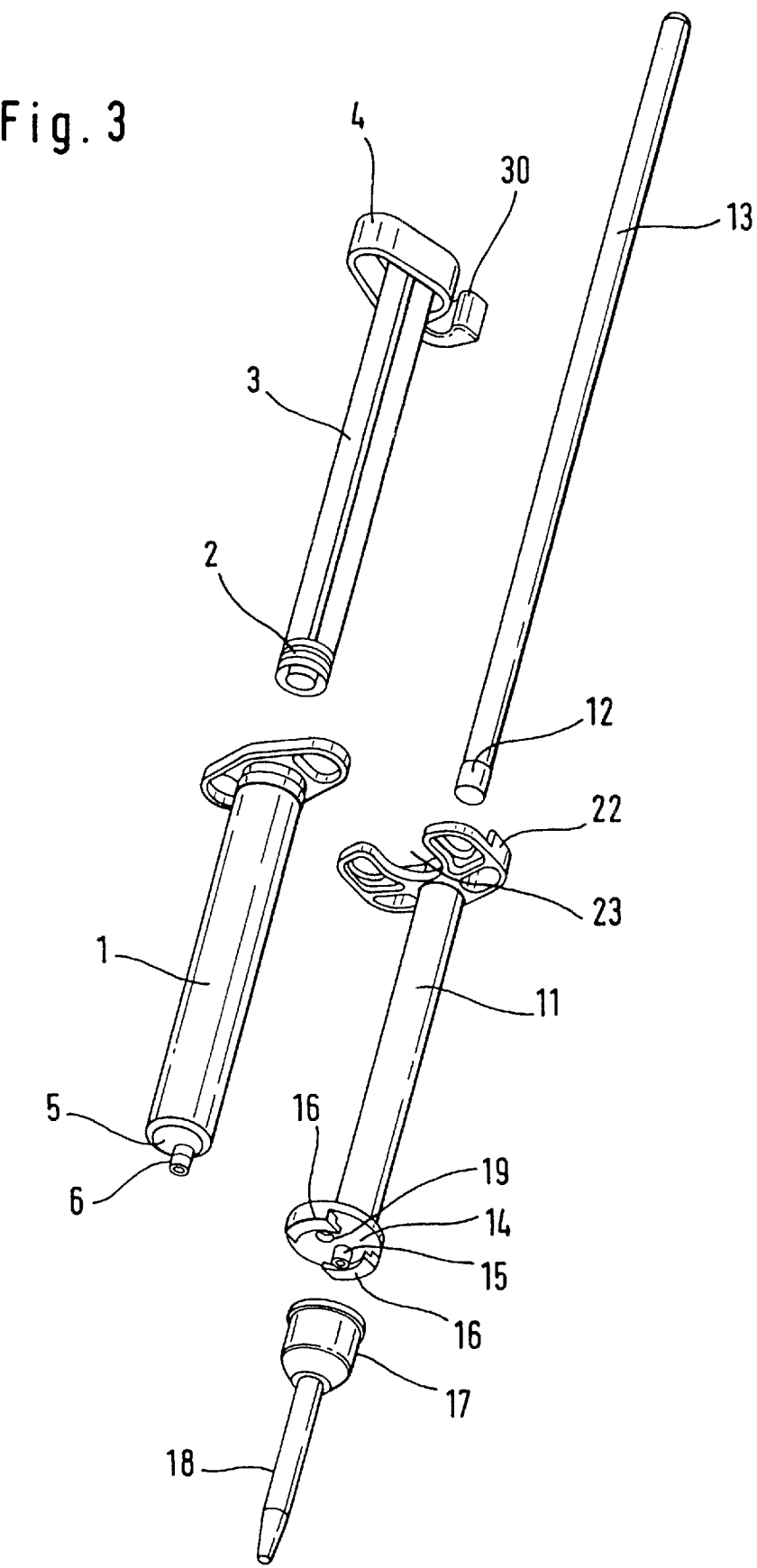
FIG. 3 shows a dismantled drawing of the first and second syringes.

FIGS. 1 to 3 show a first syringe having a syringe body 1, piston 2, piston rod 3 and piston rod head 4. The syringe body consists of a hollow cylinder, which is closed at the front end by a front plate 5 from which a release pipe 6 rises. If the first syringe is used alone, a nozzle 7 is applied to the release pipe 6.

According to FIG. 2, the first syringe is assembled with a second syringe having a syringe body 11, a piston 12 and a piston rod 13 connected thereto which is approximately twice as long as the piston rod 3. The piston need not differ in diameter from the piston rod. It may, for example, be formed by a sealing ring or a sealing edge. In the simplest case, the piston is formed by the end surface and end edge of an unjointed rod of constant diameter.

Located at the front end of the syringe body 11 is a stop plate 14, from the underside of which the release pipe 15 associated with the syringe body 11 projects. In addition, the stop plate 14 possesses mountings 16 at the front for the head 17 of a release nozzle 18.

The release pipe 15 is seated eccentrically in the stop plate 14 relative to the mountings 16. The stop plate 14 contains, symmetrically with the release pipe 6, a drilled hole 19 whose diameter is no greater, or little greater, than the external diameter of the release pipe 6 for the first syringe. When the syringe body 1 of the first syringe is attached to the syringe body 11 of the second syringe, the release pipe 6 of the first syringe body 1 is pushed through the drilled hole 19, so that it protrudes parallel to the release pipe 6 of the second syringe. The head 17 of the nozzle 18 is so formed that it can be connected in a known manner, of no concern here, to the two release pipes 6, 15 and can be fixed in the connected position by the mountings 16.

When the release pipe 6 of the syringe body 1 is pushed through the drilled hole 19, the end surface 5 of the syringe body 1 lies on the rear surface of the stop plate 14, as is shown in FIG. 2. The axial position of the syringe body 1 is then determined by the interaction of the end surface 5 with the rear surface of the stop plate 14.

Provided at the rear end of the syringe body 11 is a forked plate 22, whose arms enclose an intermediate space 23 that fits the diameter of the syringe body 1. More precisely, the width of the intermediate space 23 fits the diameter of an annular groove 24 at the rear end of the syringe body 1, whose axial length corresponds to the axial thickness of the arms of the forked plate 22. If, after the release pipe 6 has been inserted into the drilled hole 19, the syringe body 1 is swung towards the syringe body 11, the arms of the armed plate 22 enter into the retaining groove 24 and form stops interacting with the flanks thereof which—jointly with the stop plate 14 or otherwise—determine the axial position of the syringe body 1 relative to the syringe body 11 to within a close tolerance.

In order for the syringe bodies to remain in this position, the arms of the forked plate 22 may be formed as a snap-fit mounting, so that the syringe body 1 can leave the coupled position only by overcoming a force threshold. However, this is in some cases not necessary if the connection of the coupling rods secures the syringes in the desired position.

It will be understood that the snap-fit mounting provided at the rear of the syringe bodies in the example may also be disposed at the front, or both ends of the syringe bodies may be provided with snap-fit mountings. It is also possible to use the device for connecting a release or mixing nozzle to the syringe bodies to couple the latter. For example, a hasp-type mounting may be used which grips both syringe bodies, mutually supplementary parts (for example, forming equal halves) of the syringe bodies forming the counterpiece to the hasp-type mounting. The hasp-type mounting may (in contrast to the syringes and nozzles) be designed as a reusable part made, for example, from metal.

The piston rod head 4 of the first syringe is so formed on one side that it is suitable in a known manner as a pressure plate for the use of this syringe alone. It is also provided on the other side with a hook 30 whose central distance from the piston rod 3 is equal to the central distance apart of the coupled syringe bodies 1, 11. The hook 30 is formed as a clamp to receive the piston rod 13, which can be snapped into the hook space after slight elastic deformation of the hook. The force whereby the hook 30 clamps around the piston rod 13 is so great that the friction generated thereby in the direction of advance between these parts is greater than the resistance encountered by the piston 12 in releasing the composition contained in the syringe body 11. This means that when pressure is exerted on the piston rod head 4, the two pistons can be advanced while rigidly connected to one another. As the hook 30 can be hooked onto the piston rod 13 at any axial point, the coupling of the pistons is not dependent on their respective positions of advance. It is merely necessary to ensure that when the coupling connections between the hook 30 and the piston rod 13 are closed, both pistons rest on the composition to be released, with no intermediate space.

If it is again desired to use the first syringe alone or in combination with another second syringe, the coupling devices can readily be released again.

In order for the hook 30 not to slip on the piston rod 13, the surface of the piston rod 13 and/or the inner surface of the hook 30 is/are expediently roughened or transversely grooved or ribbed.

Figure 4:
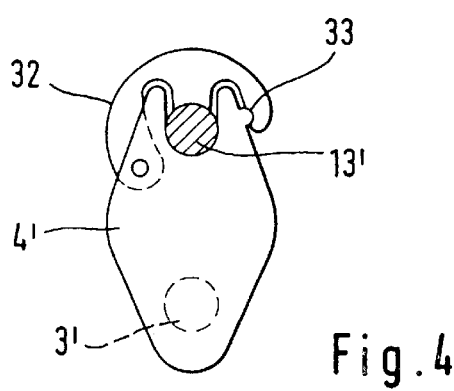
FIGS. 4 and 5 show a coupling device for piston rods in two different functional positions.
Figure 5:
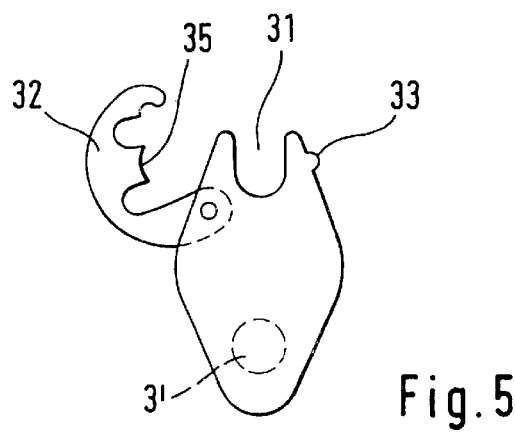

It will be understood that the elastic clamp formed by the hook 30 can be replaced with other structural forms that serve the same function. For example, if the clamping force of the hook 30 is insufficient, it can be formed with an additional clamping device, as is shown in FIGS. 4 and 5. Instead of the hook 30, a fork-shaped recess 31 for the piston rod 13 is present at the head 4' of the piston rod 3', which can be closed by a shackle 32 which is retained in the closed position by means of a snap lock 33 and, in that position, increases the pressure on the piston rod 13 by means of a shackle part 35 and/or compresses the fork parts that limit the space 31.

Figure 6:
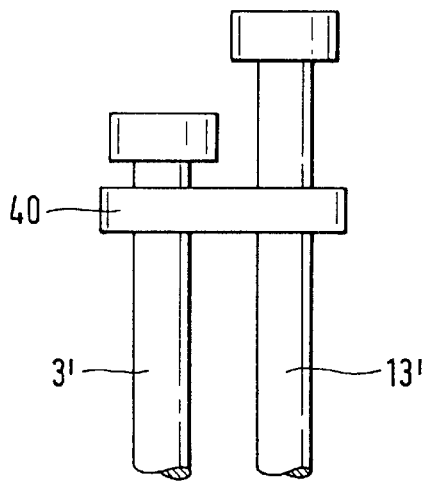
FIGS. 6 to 8 show a further embodiment of a clamp for connecting piston rods.
Figure 7:
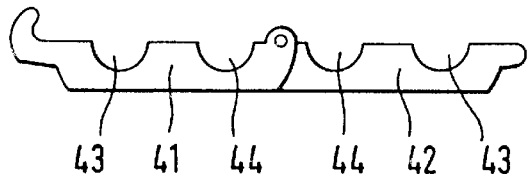
Figure 8:
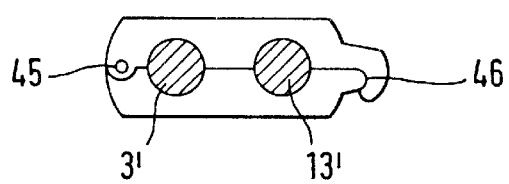

The greater length of the piston rod 13 by comparison with the piston rod 3 can be dispensed with if a special clamp is used to connect the piston rods, as is shown in FIGS. 6 to 8. For the connection of the piston rods 3', 13', the clamp 40 is provided, consisting of two folding halves 41, 42 which enclose between them receiving apertures 43, 44 for, in each case, one piston rod 3', 13', when they are closed. They are connected to one another on one side by means of a hinge 45 and at the other end by means of a snap closure 46.

Figure 9:
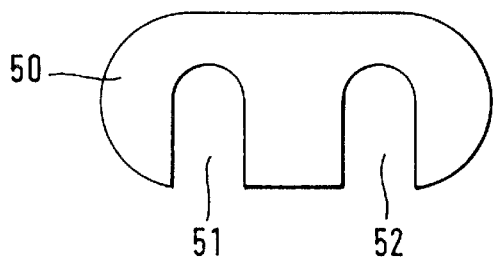
FIG. 9 shows a further embodiment for connecting two piston rods.

A very simple coupling member is shown in FIG. 9, specifically a disc 50 having two parallel, U-shaped cut-outs 51, 52, the width of each of which is matched to a piston rod so that it can be pushed onto the piston rods from the side with elastic deformation and corresponding clamping stress at any desired point.

Finally, FIGS. 10 to 12 show a final embodiment of coupling devices. Each syringe body 60, 61 is provided or one side with a rib 62 and on the other side with a groove 63 matching the latter and formed by projecting groove flanks. The cross section is illustrated in FIG. 12 (section along the line XII—XII). The piston rods 64, 65, which are grooved in the circumferential direction, bear piston rod heads 67, 68, which have the shape shown in FIG. 10 (section along line X—X). They have a unilateral projection which bears a semicircular recess 69 at the end, whose center point 70 is as far from the central axis 71 of the associated piston rod 65 as the central axes of the piston rods 64, 65 are from one another, or slightly more. The surface of the recess 69 is grooved in the same way as the piston rods 64, 65. When the two syringe bodies 60, 61 are coupled to one another, it is necessary to ensure that the piston rod head 67 nearest to its syringe body is facing the adjacent piston rod 64, so that the latter is received by the recess 69 and interacts with the latter with positive fitting in the direction of advance. During use, the syringe bodies are held in a manner such that the coupling connection is maintained both between the syringe bodies and between the piston rods.

A touch-and-close fastener may also be used to connect the syringe bodies and/or the piston rods.

The invention makes it possible to use a syringe optionally with or without additional syringes to be used to release equal proportions, without the same level of filling being important. Thus, for example, dental materials can have different curing mechanisms, different consistencies, different setting times or different colorations, depending on the type of the additional component. Also, the additional component may contain active substances that vary in accordance with the area of application, such as antibiotics, acids or fillers that set in the absence of fluoride. The concentration of an active substance can also be varied in this way.

The invention is not restricted to the joint use of two syringes. In the same way, three or more syringes can also be connected to one another for synchronous actuation.

What is claimed is:

1. System for the release of equal proportions of two or more flowable substances from two or more syringes, each having a body and a piston and piston rod defining a direction of advance with respect to said body of which at least one syringe is also used alone or in combination with other syringes, especially for dental purposes, which system comprises detachable devices for coupling the syringe bodies and the syringe pistons rigidly in the direction of advance, characterized in that the pistons or their piston rods can be coupled to one another in the direction of advance in any desired relative position irrespective of the current position of the piston.

2. System according to claim 1, characterized in that the syringe bodies can be coupled to one another in the direction of advance only in a predetermined relative position.

3. System according to claim 2, characterized in that the device for coupling the syringe bodies is fixedly connected to at least one syringe body.

4. System according to claim 3, characterized in that a part of the device for coupling the syringe bodies is formed as a stop for a frontal surface of the syringe body counter to the direction of advance.

5. System according to claim 3, wherein at least one syringe body has a release pipe characterized in that the device for coupling the syringe bodies is also formed to localize the release pipe of at least one of the two syringe bodies transversely to the direction of advance.

6. System according to claim 3, characterized in that the device for coupling the syringe pistons is formed as a device for coupling piston rods connected to the pistons.

7. System according to claim 2, wherein at least one syringe body has a release pipe characterized in that the device for coupling the syringe bodies is also formed to localize the release pipe of at least one of the two syringe bodies transversely to the direction of advance.

8. System according to claim 7, characterized in that the part of the coupling device localizing at least one release pipe is provided with a nozzle for the joint release and optional mixing of the two substances.

9. System according to claim 8, characterized in that the device for coupling two syringe bodies comprises a part forming a stop counter to the direction of advance and a more rearward part which forms a stop in the opposite direction.

10. System according to claim 9, characterized in that the more rearward part of the coupling device is provided with a snap-fit mounting acting transversely to the direction of advance.

11. System according to claim 7, characterized in that the part of the coupling device localizing at least one release pipe is provided with a device for the releasable retention of a nozzle for the joint release and optional mixing of two substances.

12. System according to claim 2, characterized in that a part of the device for coupling the syringe bodies is formed as a stop for a frontal surface of the syringe body counter to the direction of advance.

13. System according to claim 2, characterized in that the device for coupling the syringe pistons is formed as a device for coupling piston rods connected to the pistons.

14. System according to claim 1, characterized in that a part of the device for coupling the syringe bodies is formed as a stop for a frontal surface of the syringe body counter to the direction of advance.

15. System according to claim 14, wherein at least one syringe body has a release pipe characterized in that the device for coupling the syringe bodies is also formed to localize the release pipe of at least one of the two syringe bodies transversely to the direction of advance.

16. System according to claim 1, characterized in that the device for coupling the syringe pistons is formed as a device for coupling piston rods connected to the pistons.

17. System according to claim 16, characterized in that a clamp is fixedly connected to the piston rod of a one of the syringes in the direction of advance to grip the piston rod of another of the syringes.

18. System according to claim 17, wherein each clamp has a surface characterized in that the piston rods and the surface of the clamps interacting therewith are formed to engage into one another.

19. System according to claim 16, characterized in that a separate second clamp is provided to connect the two piston rods.

20. System according to claim 19, wherein each clamp has a surface characterized in that the piston rods and the surface of the clamps interacting therewith are formed to engage into one another.

* * * * *